(12) United States Patent
Meyer et al.

(10) Patent No.: US 9,427,385 B2
(45) Date of Patent: Aug. 30, 2016

(54) POLYGLYCEROL ESTERS WITH A PARTICULAR OLIGOMER DISTRIBUTION OF THE POLYGLYCEROL

(71) Applicant: Evonik Industries AG, Essen (DE)

(72) Inventors: Juergen Meyer, Essen (DE); Achim Friedrich, Hattingen (DE); Hannelore Foetsch, Essen (DE); Oliver Springer, Wesel (DE); Jan Marian von Hof, Essen (DE); Hans Henning Wenk, Muelheim an der Ruhr (DE)

(73) Assignee: EVONIK DEGUSSA GMBH, Essen (DE)

( * ) Notice: Subject to any disclaimer, the term of this patent is extended or adjusted under 35 U.S.C. 154(b) by 83 days.

(21) Appl. No.: 14/019,024

(22) Filed: Sep. 5, 2013

(65) Prior Publication Data

US 2014/0072521 A1  Mar. 13, 2014

(30) Foreign Application Priority Data

Sep. 5, 2012 (DE) .................. 10 2012 215 707

(51) Int. Cl.
| | | |
|---|---|---|
| *C07C 69/604* | (2006.01) | |
| *A61K 8/37* | (2006.01) | |
| *A61Q 17/04* | (2006.01) | |
| *A61Q 19/00* | (2006.01) | |
| *B01F 17/00* | (2006.01) | |
| *C07C 69/33* | (2006.01) | |
| *A61Q 5/12* | (2006.01) | |
| *A61Q 19/04* | (2006.01) | |
| *C07C 67/08* | (2006.01) | |
| *A61K 8/85* | (2006.01) | |
| *A61Q 15/00* | (2006.01) | |

(52) U.S. Cl.
CPC ... *A61K 8/37* (2013.01); *A61K 8/85* (2013.01); *A61Q 5/12* (2013.01); *A61Q 17/04* (2013.01); *A61Q 19/00* (2013.01); *A61Q 19/04* (2013.01); *B01F 17/0028* (2013.01); *C07C 67/08* (2013.01); *C07C 69/33* (2013.01); *C07C 69/604* (2013.01); *A61Q 15/00* (2013.01); *A61Q 19/005* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 7,906,664 B2 | 3/2011 | Allef et al. | |
| 7,910,119 B2 | 3/2011 | Allef et al. | |
| 8,211,972 B2 | 7/2012 | Meyer et al. | |
| 8,227,399 B2 | 7/2012 | Wenk et al. | |
| 8,466,248 B2 | 6/2013 | Meyer et al. | |
| 8,653,289 B2 * | 2/2014 | Wenk et al. | 554/227 |
| 2004/0258649 A1 | 12/2004 | Peggau et al. | |
| 2007/0092470 A1 | 4/2007 | Allef et al. | |
| 2007/0178144 A1 | 8/2007 | Hameyer et al. | |
| 2008/0004357 A1 | 1/2008 | Meyer et al. | |
| 2008/0108709 A1 | 5/2008 | Meyer et al. | |
| 2010/0184733 A1 | 7/2010 | Korevaar et al. | |
| 2010/0266651 A1 | 10/2010 | Czech et al. | |
| 2011/0300082 A1 * | 12/2011 | Wenk et al. | 424/59 |
| 2012/0308503 A1 | 12/2012 | Wenk et al. | |
| 2012/0309667 A1 | 12/2012 | Wenk et al. | |
| 2013/0071340 A1 | 3/2013 | Wenk et al. | |

FOREIGN PATENT DOCUMENTS

| | | |
|---|---|---|
| DE | 102008001788 A1 | 11/2009 |
| EP | 1623694 A1 | 2/2006 |
| JP | 2003104852 | 4/2003 |
| JP | 200655029 | 3/2006 |
| JP | 2010178723 | 8/2010 |
| WO | WO2008103289 | 8/2008 |
| WO | WO2011098311 | 8/2011 |
| WO | WO2012127129 | 9/2012 |

OTHER PUBLICATIONS

European Search Report dated Apr. 23, 2015, received in a corresponding foreign application.
Finkel, P., et al., "Formulierung Kosmetischer Sonnenschutzmittel", 1996, SÖFW-journal, vol. 122, p. 543, With English-Language Abstract.
Schrader, K. et al., "Grundlagen and Rezepturen der Kosmetika" ["Principles and Formulations of Cosmetics"], 1989, 2nd edition, p. 329 to 341, Hüthig Buch Verlag Heidelberg.

* cited by examiner

*Primary Examiner* — Brian Gulledge
(74) *Attorney, Agent, or Firm* — Scully, Scott, Murphy & Presser, P.C.

(57) ABSTRACT

The invention relates to polyglycerol esters with a particular oligomer distribution of the polyglycerol present, and to their use in in particular cosmetic formulations as, for example, emulsifier.

12 Claims, 2 Drawing Sheets

POLYGLYCEROL ESTERS WITH A PARTICULAR OLIGOMER DISTRIBUTION OF THE POLYGLYCEROL

FIELD OF THE INVENTION

The present invention relates to polyglycerol esters with a particular oligomer distribution of the polyglycerol, and to the use of such polyglycerol esters in cosmetic formulations, preferably as emulsifier.

PRIOR ART

In recent years in the cosmetics market there has been a strong trend towards pursuing products based on renewable raw materials. In order to be able to satisfy this, it is necessary to be able to offer high-performance emulsifiers based on renewable raw materials. Customary emulsifiers in cosmetics often contain polyethylene glycol groups (PEG) as hydrophilic groups; these can be prepared by polymerization of petrochemically obtained ethylene oxide. Since in formulations that are as natural as possible all of the raw materials used should stem from renewable resources, PEG-containing emulsifiers are undesired in such formulations.

Polyglycerol esters are preferred PEG-free alternatives for cosmetic emulsifiers based on renewable raw materials.

The use of polyglycerol esters in cosmetics as emulsifier is well known in the art.

For example, JP 2003104852 describes the use of a polyglycerol-benhenate-stearate, which is solid at room temperature, in hair care products.

JP 2010178723 describes the use of polyglycerol partial esters of behenic acid in conjunction with other, shorter-chain fatty acids as dough improvers in bakery groups.

JP 2006055029 describes the use of triglycerol-monobehenate-monostearate in crop protection applications.

With the polyglycerol esters described in the prior art, it is not possible to produce stable emulsions with a good skin feel despite low viscosity, especially in conjunction with high concentrations of emulsion-burdening ingredients, such as, for example, electrolytes, active ingredients, UV filters or preservatives.

SUMMARY OF THE INVENTION

The present invention provides polyglycerol esters which, after complete hydrolysis, release on an average (number-average) per mole of polyglycerol ester, from 0.51 to 2.20 mol of at least one carboxylic acid having 8 to 24 carbon atoms. The polyglyerol esters of the present invention are further characterized in that, after complete hydrolysis of the polyglycerol ester, a polyglycerol is obtained in which the mass ratio of glycerol to diglycerol is greater than 1.

The present invention also provides a process for producing such polyglycerol esters. Moreover, the present invention provides the use of the inventive polyglycerol esters as emulsifier and formulations which comprise the polyglycerol esters of the present invention.

One advantage of the present invention is that the provided emulsifier based on the polyglycerol ester according to the invention is based entirely on renewable raw materials.

Another advantage of the present invention is that the provided emulsifier based on the polyglycerol ester according to the invention is suitable for formulating O/W emulsions (creams, lotions) with exceptional storage stability.

A further advantage of the present invention is that the provided emulsifier based on the polyglycerol ester according to the invention is suitable for formulating PEG-free emulsions, in particular thin-liquid PEG-free emulsions.

Emulsions and formulations comprising such an emulsifier based on the polyglycerol ester according to the invention have a good skin feel.

The emulsifier based on the polyglycerol ester of the present invention can stabilize emulsions against emulsion-burdening ingredients. Mention is made here, for example, of sunscreen formulations comprising UV filters, electrolyte-containing formulations and formulations with cosmetic active ingredients, and also in particular pigment-containing emulsions.

Advantageously, emulsions and formulations comprising such an emulsifier based on the polyglycerol ester according to the invention require no paraben-containing preservatives.

Another advantage of the present invention is that the provided emulsifier is suitable for formulating emulsions without polyacrylate-based thickeners.

An even further advantage of the present invention is that the provided emulsifier is easy to handle on account of its consistency.

A yet even further advantage of the present invention is that the provided emulsifier produces a light skin feel in formulations.

A still further advantage of the present invention is that the use of the provided emulsifier imparts moistening properties to the formulations.

The composition of natural raw materials and the ability of the emulsifier based on the polyglycerol ester according to the invention to stabilize emulsions even without polyacrylate-based thickeners permits the production of natural emulsions for example according to Nature or Cosmos criteria. The light skin feel and the moisturizing properties of the polyglycerol emulsifiers according to the invention advocate the use of these in sera, moisturizing lotions, anti-ageing formulations or blemish balm creams (tinted active ingredient formulation).

It is a further advantage of the present invention that the use of the provided emulsifier gives the formulations good effectiveness as regards incorporated insect repellents specifically in combination with UV filters, in particular water-soluble UV filters.

It is a further advantage of the present invention that the use of the provided emulsifier gives the formulations good stability as regards incorporated insect repellents specifically in combination with UV filters, in particular water-soluble UV filters.

DETAILED DESCRIPTION

The present application will now be described in greater detail by referring to the following discussion and examples that accompanying the present application.

According to an embodiment of the present application, a polyglycerol ester is provided which, after its complete hydrolysis, releases on an average (number-average) per mole of polyglycerol ester, from 0.51 to 2.20 mol, preferably from 0.73 to 1.85 mol, particularly preferably from 0.85 to 1.50 mol, of at least one carboxylic acid having 8 to 24 carbon atoms. The polyglycerol ester of the present invention is further characterized in that, following complete hydrolysis of the polyglycerol ester, a polyglycerol is obtained in which the mass ratio of glycerol to diglycerol is greater than 1, preferably greater than 1.2, particularly preferably greater than 1.5.

Preferred polyglycerol esters according to the invention are characterized in that, following their complete hydrolysis, on average (number-average) per mole of polyglycerol ester, from 0.01 to 0.20 mol, preferably from 0.03 to 0.15 mol, particularly preferably from 0.05 to 0.10 mol, of at least one first carboxylic acid having 20 to 24 carbon atoms and from 0.5 to 2.0 mol, preferably from 0.7 to 1.7 mol, particularly preferably from 0.8 to 1.4 mol, of at least one second carboxylic acid having 8 to 18, preferably having 14 to 18, particularly preferably from 16 to 18, carbon atoms, are released.

Within the context of the present invention, the term "polyglycerol" is to be understood as meaning a polyglycerol which contains glycerol. Consequently, to calculate amounts, masses and the like, the fraction of glycerol should be taken into consideration. Within the context of the present invention, polyglycerols are thus mixtures of glycerol with at least one glycerol oligomer.

In connection with the present invention, the same applies to the term "polyglycerol ester".

The stated number-average of the acid radicals refers, in the event of more than one of the first and/or second carboxylic acid, in each case to the accumulated sum of all of the first and/or second acid radicals.

Unless stated otherwise, all of the stated percentages (%) are percentages by mass.

The mass ratio of glycerol to diglycerol and also the other homologue distribution of the polyglycerol can be determined in the course of the present invention according to the GPC method; this method involves the alkaline hydrolysis of the polyglycerol ester according to the invention, separation of the polyglycerol from the resulting acids and analysis by gel permeation chromatography.

For this purpose, 0.6 g of the polyglycerol ester according to the invention is boiled under reflux for 4 hours in 25 ml of an ethanolic 0.5 M KOH solution. The pH is then adjusted to pH 2-3 with sulphuric acid, and the resulting carboxylic acids are separated off by triple extraction with one volume of petroleum ether in each case. The combined extracts are concentrated by evaporation to ca. 10 ml.

Suitable determination methods for ascertaining the fatty acid distribution are those according to DGF C VI 11a, DGF C-VI 10 a and GAT—ringtest 7/99.

A 0.5 ml aliquot of the petroleum ether extract obtained as described above is admixed in an autosampler vessel with 0.5 ml of MTBE and 1 ml of trimethylaniliniumhydroxide (0.2 M in methanol) and analysed by means of GC. This is carried out in a gas chromatograph, which is equipped with a split/splitless injector, a capillary column and a flame ionization detector, under the following conditions:

Injector: 290° C., split 30 ml
Injection volume: 1 µl
Column: 30 m*0.32 mm HP1 0.25 µm
Carrier gas: Helium, head pressure 70 kPa
Temperature programme: 80° C.-300° C. at 8° C./min, then condition for 20 minutes at 300° C.
Detector: FID at 320° C.
Hydrogen 35 ml/min
Air240 ml/min
Make-up gas 12 ml/min The carboxylic acids are separated as their methyl esters according to their carbon chain length. By evaluating the peak areas, the mass ratio of these carboxylic acid methyl esters with one another can be determined and, by means of their respective molecular weights, their quantitative ratio can be determined therefrom, which corresponds to the quantitative ratio of the relevant carboxylic acids. Moreover, an average molecular weight of this fatty acid mixture can be determined:

$$a_i = \frac{A_i}{\sum_i A_i} \cdot 100$$

where $a_i$ = Standardized mass fraction of the carboxylic acid methyl ester i in the mixture of all carboxylic acid methyl esters [%].
$A_i$ = Peak area of the carboxylic acid methyl ester i in the GC chromatogram [%].

$$n_i = \frac{a_i}{(M_i + 14)}$$

where $n_i$ = Quantitative amount [mol] of the carboxylic acid methyl ester i in 100 g of carboxylic acid methyl ester mixture; this is used to obtain the ratios of the individual $n_i$ among one another, which correspond to the quantitative ratios of the relevant carboxylic acids in the polyglycerol ester; the total quantitative amount $n_s$ [mol] of the carboxylic acids in 1 g of polyglycerol ester, as obtained from the saponification value (see below), can be divided into their components according to the ratios.
$M_i$ = Molecular weight of the carboxylic acid i corresponding to the methyl ester [g/mol].

$$\overline{M_s} = \sum_i \left( \frac{n_i}{\sum_i n_i} \cdot M_i \right)$$

where $\overline{M_s}$ = Average molecular weight of the carboxylic acid mixture.
$n_i$ = Quantitative amount [mol] of the carboxylic acid methyl ester i in 100 g of carboxylic acid methyl ester mixture.
$M_i$ = Molecular weight of the carboxylic acid i [g/mol].

Suitable determination methods for ascertaining the saponification value include DGF C-V 3 and Ph. Eur. 2.5.6.

Using the saponification value, moreover, it is possible firstly to obtain the total quantitative amount of carboxylic acid(s) present in 1 g of polyglycerol esters and then (by means of the quantitative amount ratio determined as described above by GC analysis and the molecular weights of the carboxylic acids) the total mass of carboxylic acid(s). From this, in turn, it is possible to determine, by subtraction, the mass of polyglycerol present in 1 g of polyglycerol ester:

$$\frac{SV}{1000 \cdot 56.11} = n_s$$

where SV = Saponification value [mg KOH/g polyglycerolesters].
$n_s$ = Total quantitative amount [mol] of the carboxylic acids in 1 g of polyglycerol esters.

-continued $$\frac{1 - (\overline{M_s} \cdot n_s - n_s \cdot 17) + n_s \cdot 1}{m_p} = \quad \text{where } \overline{M_s} = \text{Average molecular weight of the carboxylic acid mixture [g/mol]}.$$
$n_s$ = Total quantitative amount [mol] of the carboxylic acids in 1 g of polyglycerol esters.
$m_p$ = Mass of polyglycerol in 1 g of polyglycerol esters [g].

Using the molecular weight of the polyglycerol it is possible to determine the quantitative amount of the polyglycerol:

$M_p = 74 \cdot N + 18$ where $M_p$ = Molecular weight of the polyglycerol [g/mol]
N = Degree of polymerization of the polyglycerol (to determine the degree of polymerization see below).

$n_p = \dfrac{m_p}{M_p}$ where $n_p$ = Quantitative amount of the polyglycerol [mol] in 1 g of polyglycerol ester
$m_p$ = Mass of polyglycerol in 1 g of polyglycerol esters [g]
$M_p$ = Molecular weight of the polyglycerol [g/mol]

Together, these values can be used to determine the molar ratios of polyglycerol to carboxylic acids.

The residue extracted with petroleum ether is adjusted to pH 7 to 8 with barium hydroxide. The precipitated barium sulphate is separated off by centrifugation. The supernatant is removed and the residue is extracted three times with 20 ml of ethanol.

The combined supernatants are concentrated by evaporation for 30 min at 80° C. and 50 mbar and dried.

For the analysis of the polyglycerol fraction by means of GPC, a sample concentration of 1 g/l in the eluent, $H_2O$ with 0.05% $NaN_3$ is prepared from the residue. One aliquot is analysed under the following conditions:
Instrument: Pump: Agilent 1200, isocratic
  Autosampler Agilent 1100
Detector: Agilent R1
Sample concentration: 1000 g/L
Injection volume: 50 000 μL
Column: SUPREMA 30 Å, 8 mm×300 mm and precolumn
Flow rate: 0.5 mL/min
Column temperature: 30° C.
Software for Analysis: PSS WinGPC Unity Version 7.5.0

Under these conditions, the polyglycerol is separated according to the degree of polymerization. Since the resolution of the different oligomers is low and the determination of the peak areas of the individual oligomers through a perpendicular in the minimum between the peaks is too imprecise, the relative content of the individual oligomers (primarily glycerol and diglycerol) is determined by evaluating the peak heights.

Should no detectable amount of diglycerol, but glycerol be present in a polyglycerol under consideration, then this corresponds to a mass ratio of glycerol to diglycerol of greater than 1.2.

According to the invention, it is preferred that the polyglycerol obtained following complete hydrolysis of the polyglycerol ester according to the invention has an average degree of polymerization of from 3 to 20, preferably from 3.5 to 15, particularly preferably from 4.5 to 10.

The average degree of polymerization of the polyglycerol, N, is calculated via its hydroxyl value (OHV, in mg KOH/g) according to the following formula:

$$N = \frac{(112200 - 18 \cdot OHV)}{(74 \cdot OHV - 56100)}$$

Suitable determination methods for ascertaining the hydroxyl value are those in accordance with DGF C-V 17 a (53), Ph. Eur. 2.5.3 Method A and DIN 53240.

Advantageous polyglycerol esters according to the present invention are characterized in that the molar ratio of the first carboxylic acids obtained after complete hydrolysis of the polyglycerol ester relative to the second carboxylic acid is between 1:50 and 1:7, preferably between 1:28 and 1:10, particularly preferably between 1:19 and 1:13.

To determine the molar ratios, the method used can be that described above.

A polyglycerol ester according to the invention is characterized in that the first carboxylic acid contains 20 to 24 carbon atoms and the second carboxylic acid contains 8 to 18 carbon atoms.

According to the invention, it is preferred that the first and second carboxylic acids of the polyglycerol ester is selected from fatty acids, these being in particular selected from linear, saturated, unsubstituted carboxylic acids.

The fatty acids which can be used both for the first and the second carboxylic acids, are mixtures of fatty acids, it being preferred for the second carboxylic acid that it is a mixture in this connection. This has its roots in the nature of the production process, in which industrial mixtures of fatty acids are preferably used.

A polyglycerol ester preferred according to the invention is characterized in that it comprises, as the first carboxylic acid, one selected from arachic acid, behenic acid and lignoceric acid, particularly preferably behenic acid. Additionally, monoolefinic unsaturated carboxylic acids are also suitable as the first carboxylic acid, e.g., eicosenic acid and docosenic acid such as gadoleic acid, icosenic acid, cetoleic acid, erucacic acid, brassidic acid, and nervonic acid.

Preferred second carboxylic acids are lauric acid, tridecanoic acid, myristic acid, palmitic acid, margaric acid, stearic acid, isostearic acid, and mixtures thereof.

Naturally occurring mixtures are, for example, coconut fatty acids which contain as the main constituent lauric acid, in addition saturated $C_{14}$-$C_{18}$-fatty acids and optionally saturated $C_8$-$C_{10}$-fatty acids and unsaturated fatty acids. In this connection, palmitic acid and stearic acid are the particularly preferred second carboxylic acid. These can be present as a mixture which can be broadly varied in the weight ratio of stearic acid to palmitic acid from 100:0.01 to 0.01:100. Preference is given in this connection to a C18:C16 weight ratio of 30:70 to 95:5, particularly a ratio of 45:55 to 90:10.

Additionally, the monoolefinically unsaturated carboxylic acids are also suitable as the second carboxylic acid, for example hexadecenoic acids, octadecenoic acids, such as oleic acid (cis-9-octadecenoic acid) or elaidic acid (trans-9-octadecenoic acid), and also the polyunsaturated fatty acids, for example, octadecadienoic acids and octadecatrienoic acids, such as linoloic acid and linolenoic acid, and mixtures thereof.

A particularly preferred embodiment of the polyglycerol ester according to the invention is characterized in that the first carboxylic acid is behenic acid and the second carboxylic acid is a mixture of stearic acid and palmitic acid, which preferably has a weight ratio in a range from 0.8:1 to 1.2:1.

It is preferred according to the invention that the polyglycerol ester according to the invention has a melting point of greater than 35° C., preferably greater than 40° C., in particular greater than 50° C. The melting point of the polyglycerol ester can be influenced, for example, by varying the content of long-chain, saturated fatty acids (see for example Ullmanns Encyclopaedia of Industrial Chemistry or Römpp Lexicon of Chemistry, in each case relating to fatty acids).

The polyglycerol esters of the present invention can be prepared by classic esterification processes, preferably with the process according to the invention described below.

The present invention further provides a process for producing a polyglycerol ester comprising the process steps
A) provision of a polyglycerol in which the mass ratio of glycerol to diglycerol is greater than 1, preferably greater than 1.2, particularly preferably greater than 1.5, and
B) esterification of at least some of the polyglycerol with at least one carboxylic acid having 8 to 24 carbon atoms, where the molar ratio of the carboxylic acid used in process step B) to polyglycerol used in process step A) is from 0.51:1 to 2.20:1, preferably from 0.73:1 to 1.85:1, particularly preferably from 0.85:1 to 1.5:1.

Preferred processes according to the invention are characterized in that, in process step B) at least one first carboxylic acid having 20 to 24 carbon atoms and at least one second carboxylic acid having 8 to 18 carbon atoms is used, where the molar ratio of the first carboxylic acid used in process step B) to polyglycerol used in process step A) is from 0.01:1 to 0.20:1, preferably from 0.03:1 to 0.15:1, particularly preferably from 0.05:1 to 0.10:1, and the molar ratio of the second carboxylic acid used in process step B) to polyglycerol used in process step A) is from 0.5:1 to 2.0:1, preferably from 0.7:1 to 1.7:1, particularly preferably from 0.8:1 to 1.4:1.

The polyglycerol for process step A) can be provided by various conventional methods such as, for example, polymerization of glycidol (e.g., base-catalysed), polymerization of epichlorhydrin (for example, in the presence of aquimolar amounts of a base such as NaOH) or polycondensation of glycerol.

According to the invention, preference is given to provision of the polyglycerol via the condensation of glycerol, in particular in the presence of catalytic amounts of a base, in particular NaOH or KOH. Suitable reaction conditions are temperatures between 220-260° C. and reduced pressure in a range between 20 and 800 mbar, in particular between 50 and 500 mbar, as a result of which easier water removal is possible. Appropriate methods can be found in standard chemistry textbooks such as, for example, Römpp.

It may be advantageous to convert a conventionally obtained polyglycerol to the ratio of glycerol to diglycerol required according to the invention by admixing it with glycerol.

It is preferred if the polyglycerol provided in process step A) has an average degree of polymerization of from 3 to 20, preferably from 3.5 to 15, particularly preferably from 4.5 to 10.

In the process according to the invention, process step B) is carried out under conditions for esterification reactions known to the person skilled in the art, optionally in the presence of a catalyst. In particular, this esterification is carried out with the removal of water from the reaction mixture.

In one embodiment of the present invention, process step B) is carried out preferably at 180-260° C., particularly preferably 210-250° C.

The course of the reaction can be monitored for example via the acid value of the product, meaning that it is preferred in process step B) to carry this out until the desired acid value is reached.

Preferably, in process step B), the first and second carboxylic acids are used in a molar ratio between 1:50 and 1:7, preferably between 1:28 and 1:10, particularly preferably between 1:19 and 1:13. The first and second carboxylic acids used in the process according to the invention in process step B) are preferably those which have been specified as preferred in polyglycerol esters according to the invention.

In particular, in this connection, the first carboxylic acid used is behenic acid and the second carboxylic acid used is a mixture of stearic acid and palmitic acid, which preferably has a weight ratio of stearic acid to palmitic acid in a range from 0.8:1 to 1.2:1. Preferably, in this connection, first and second carboxylic acids are used in a molar ratio 1:50 to 1:7, preferably between 1:28 and 1:10, particularly preferably between 1:19 and 1:13.

Polyglycerol esters according to the invention and polyglycerol esters obtainable or obtained by the process according to the invention are exceptional suitable for use as high-performance O/W emulsifier which is based exclusively on renewable raw materials and has a large flexibility of formulation, especially in cosmetic formulations.

Consequently, emulsifiers comprising polyglycerol esters according to the invention or polyglycerol esters obtainable or obtained by the process according to the invention are provided by the present invention. Within the context of this invention, an emulsifier is to be understood as meaning an emulsifier which consists of at least one polyglycerol ester according to the invention or polyglycerol ester obtainable or obtained by the process according to the invention and optionally at least one coemulsifier, where the presence of a coemulsifier is preferred.

Coemulsifiers which can advantageously be used are the following coemulsifiers:

polyglyceryl-3 dicitrate/stearate, polyglyceryl-3 methylglucosedistearate, polyglyceryl-10 stearate, polyglyceryl-6 distearate, methylglucosesesquistearate, sodium stearoylglutamate, sodium cetearylsulphate, potassium cetylphosphate, glycerylstearate citrate, cetearylglucoside, glycerylstearate, glycerylstearate SE, cetearylalcohol and stearic acid.

Polyglycerol esters according to the invention and polyglycerol esters obtainable or obtained by the process according to the invention are likewise suitable for use for producing cosmetic or pharmaceutical formulations, in particular for producing cosmetic creams and lotions. In this connection, creams and lotions is understood as meaning cosmetic O/W emulsions with spreadable-pasty or flowable consistency. In general, the polyglycerol esters according to the invention can be used for example in care creams and lotions for the face, body and hands, in sunscreen emulsions, in sera, in BB creams, in deodorants, in makeup, in aerosols, roll-ons, pump sprays, sticks e.g., in the antiperspirant/deodorant sector, in baby care products, in intimate care, foot care, hair care, nail care, dental care and oral care products, and also in dermatological ointments.

Consequently, cosmetic or pharmaceutical formulations, in particular O/W formulations, comprising polyglycerol esters according to the invention or polyglycerol esters obtainable or obtained according to the process according to the invention are likewise provided by the present invention.

Formulations preferred according to the invention are sunscreen preparations, electrolyte-containing emulsions, formulations with cosmetic active ingredients and O/W make-up formulations.

Formulations preferred according to the invention comprise the polyglycerol ester according to the invention or polyglycerol ester obtainable or obtained according to the process according to the invention in amounts of from 0.01 to 10% by weight, preferably 0.05 to 8% by weight and particularly preferably 0.1 to 5% by weight, based on the total formulation.

In particular, cosmetic or pharmaceutical formulations are preferred which are essentially free from alkoxylated compounds. In connection with the present invention, the term "essentially free from alkoxylated compounds" is to be understood as meaning that the formulations have no noteworthy amounts of alkoxylated compounds which exert a surface-active effect. In particular, it is to be understood as meaning that these compounds are present in amounts of less than 1% by weight, preferably of less than 0.1% by weight, particularly preferably of less than 0.01% by weight, based on the total formulation, in particular no detectable amounts.

The formulations according to the invention can comprise, e.g., at least one additional component selected from the group of
  emollients,
  coemulsifiers,
  thickeners/viscosity regulators/stabilizers,
  antioxidants,
  hydrotropes (or polyols),
  solids and fillers,
  pearlescent additives,
  deodorant and antiperspirant active ingredients,
  insect repellents,
  self-tanning agents,
  preservatives,
  conditioners,
  perfume,
  dyes,
  pigments,
  cosmetic active ingredients,
  care additives,
  superfattening agents,
  solvents,
  UV filters,
  electrolytes,
  multifunctional additives,
  moisturizing substances.

Substances which can be used as exemplary representatives of the individual groups are known to the person skilled in the art and can be found, for example, in German Application DE 102008001788.4. This patent application is hereby incorporated as reference and thus forms part of the disclosure.

As regards further optional components and the amounts of these components used, reference is made expressly to the relevant handbooks known to the person skilled in the art, e.g., K. Schrader, "Grundlagen and Rezepturen der Kosmetika [Fundamentals and Formulations of Cosmetics]", $2^{nd}$ Edition, pages 329 to 341, HüthigBuchVerlag Heidelberg.

The amounts of the particular additives are governed by the intended use.

Typical guide formulations for the respective applications are known prior art and are contained, for example, in the brochures from the manufacturers of the particular base materials and active ingredients. These existing formulations can generally be used without change. If required, however, the desired modifications can be made by simple experiments without complication of adaptation and optimization.

Since the polyglycerol esters according to the invention can keep pigments or solids extremely stable in emulsion preparations, solids and fillers, particularly particles and additives which are used for achieving a specific skin feel, such as, e.g., silicone elastomers, PMMA particles, PE particles, PS particles, nylon particles, boron nitride, starch, cellulose, mica and talc, are a preferred additional component.

Emulsifiers according to the invention are particularly well suited for stabilizing low viscosity formulations (lotions) with a light skin feel. The advantage in the case of the simultaneous presence of additional emulsion-burdening formulation constituents is particularly great.

The present invention is very particularly advantageously suited for stabilizing in particular low viscosity sunscreen systems in the presence of UV filters. Consequently, a preferred cosmetic or pharmaceutical formulation comprises, as additional component, a substance selected from the group of the substances of the UV light protection filters. These can be inorganic and organic, water-soluble and oil-soluble UV filters, with the water-soluble ones being particularly preferably present.

UV filters which can be used are for example organic substances which are able to absorb ultraviolet rays and emit the absorbed energy again in the form of longer-wave radiation, e.g., heat.

UVB filters may be oil-soluble or water-soluble. Oil-soluble UVB photoprotective filters are, for example:
  3-benzylidenecamphorand derivatives thereof, e.g., 3-(4-methylbenzylidene)camphor, 4-aminobenzoic acid derivatives, such as, e.g., 2-ethylhexyl 4-(dimethylamino)benzoate, 2-ethylhexyl 4-(dimethylamino)benzoate and amyl 4-(dimethylamino)benzoate
  esters of cinnamic acid, such as, e.g., 2-ethylhexyl 4-methoxycinnamate, isopentyl 4-methoxycinnamate, 2-ethylhexyl 2-cyano-3-phenylcinnamate (octocrylene),
  esters of salicylic acid, such as e.g. 2-ethylhexyl salicylate, 4-isopropylbenzyl salicylate, homomethyl salicylate,
  derivatives of benzophenone, such as, e.g., 2-hydroxy-4-methoxybenzophenone, 2-hydroxy-4-methoxy-4'-methylbenzophenone, 2,2'-dihydroxy-4-methoxybenzophenone,
  esters of benzalmalonic acid, such as, e.g., di-2-ethylhexyl 4-methoxybenzmalonate,
  triazinederivates, such as e.g. 2,4,6-trianilino(p-carbo-2'-ethyl-1'-hexyloxy)-1,3,5-triazineand octyltriazone,
  propane-1,3-diones, such as, e.g., 1-(4-tert-butylphenyl)-3-(4'-methoxyphenyl)propane-1,3-dione.

Suitable water-soluble UVB photoprotective filters are:
  2-phenylbenzimidazole-5-sulphonic acid and the alkali metal, alkaline earth metal, ammonium, alkylammonium, alkanolammoniumand glucammonium salts thereof,
  sulphonic acid derivatives of benzophenone, such as, e.g., 2-hydroxy-4-methoxybenzophenone-5-sulphonic acid and its salts,
  sulphonic acid derivatives of 3-benzylidenecamphors, such as, e.g., 4-(2-oxo-3-bornylidenemethyl)benzenesulphonic acid and 2-methyl-5-(2-oxo-3-bornylidene)sulphonic acid and salts thereof.

Particularly preferred water-soluble UV filters are, for example, products such as Eusolex® 232 (phenylbenzimidazolessulphonicacid) (Merck KGaA) or Mexoryl® SX (terephthalylidenedicamphorsulphonicacid) (Chimex SA).

Suitable typical UVA photoprotective filters are in particular derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures. Besides the specified soluble substances, insoluble pigments, namely finely dispersed metal oxides or salts are also suitable for this purpose, such as, for example, titanium dioxide, zinc oxide, iron oxide, aluminium oxide, cerium oxide, zirconium oxide, silicates (talc), barium sulphate and zinc stearate. The particles should have an average diameter of less than 100 nm, e.g., between 5 and 50 nm and in particular between 15 and 30 nm. They can have a spherical shape, although it is also possible to use those particles which have an ellipsoidal shape or a shape that deviates in some other way from the spherical form. A relatively new class of photoprotective filters is micronized organic pigments, such as, for example, 2,2'-methylenebis{6-(2H-benzotriazol-2-yl)-4-(1,1,3,3-tetramethylbutyl)phenol} with a particle size of <200 nm, which is available, e.g., as 50% strength aqueous dispersion.

Further suitable UV photoprotective filters can be found in the review by P. Finkel in SÖFW-Journal 122, 543 (1996).

The present invention is likewise very particularly advantageously suitable for stabilizing formulations containing insect repellents, in particular in conjunction with UV photoprotective filters.

Consequently, a preferred cosmetic or pharmaceutical formulation comprises, as additional component, a substance selected from the group of the substances of the insect repellents, especially preferably as additionally at least one further additional component, a substance selected from the group of substances of the UV photoprotective filters.

Insect repellents in connection with the present invention are in particular selected from the group consisting of N,N-diethyl-m-toluamide (DEET), ethylbutylacetylaminopropionate (e.g., IR3535 from Merck Co.), hydroxyethylisobutylpiperidinecaraboxylate (1-piperidinecaraboxylic acid, e.g., Bayer KBR3023), citronella oil, soybean oil, lemon grass oil, geranium oil, dimethyl phthalate (DMP), geraniol oil and p-methane-3,8-diol or mixtures thereof, with N,N-diethyl-m-toluamide, ethylbutylacetylaminopropionate, hydroxylethylisobutylpiperidinecaraboxylate and citronella oil being particularly preferred.

The use of the emulsifier in formulations with electrolytes or ionic compounds is also an advantageous field of application. So-called multifunctional additives, which can inter alia have moisturizing, preserving, viscosity-regulating, emulsifying, stabilizing effect, can likewise be formulated very readily into O/W emulsions, particularly into lotions, using the emulsifier according to the invention, for which reason representatives of this substance group are likewise a preferred additional component.

Since the polyglycerol esters according to the invention are able to stabilize emulsions even without the use of polyacrylate-based thickeners, PEG- and/or silicone- and/or polyacrylate- and/or paraben-free formulations based on natural ingredients are a particularly preferred field of application for them.

On account of its moisturizing properties, its light skin feel and the good stabilization of cosmetic active ingredients, polyglycerol esters according to the invention are for example preferably suitable for use in cosmetic emulsions for increasing skin moisture, improving skin structure, reducing age-related skin changes, evening the complexion, promoting the skin metabolism or neutralizing harmful metabolic constituents in the skin. Consequently, moisturizing substances and substances with biological effectiveness, such as glycerol, urea, peptides, are preferred additional components in preferred formulations according to the invention.

On account of the tolerance of the emulsifiers according to the invention towards various kinds of preservatives, besides paraben-containing preservatives it is also possible to readily use paraben-free preservatives such as phenoxyethanol, ethanol or methylisothiazolinone. To produce natural cosmetics, the preservatives especially natural acids such as benzoic acid, caprylic acid, capric acid, anisic acid, sorbitanacid, levulinic acid, sorbic acid and benzoic acid or substances such as caprylylglycol are preferred preservatives, which are used as an additional formulation constituent.

In the examples listed below, the present invention is described by way of example without any intention of limiting the invention, the scope of application of which arises from the entire description and the claims, to the embodiments specified in the examples.

EXAMPLES

Example 1

A mixture of glycerol (2102 g, 22.8 mol) and 45% strength aqueous potassium hydroxide solution (24.2 g) was heated to 240° C. at 400 mbar over the course of 1 hour, and the water that formed was continuously distilled off. As soon as the reaction mixture had reached a refractive index of ≥1.4900 (typically after 20-21 h at 240° C.), the pressure was slowly lowered to 50 mbar and further water and also excess glycerol were distilled off at 240° C. until the remaining mixture had a hydroxyl value of 880 mg KOH/g.

A mixture of the polyglycerol obtained in this way (360.0 g, 0.45 mol) and glycerol (47.82 g, 0.52 mol) with a hydroxyl value of 1000 mg KOH/g and a mixture of stearic acid and palmitic acid in the ratio 1:1 (334.19 g, 1.24 mol), behenic acid (28.0 g, 0.08 mol) and $Na_2CO_3$ (3.75 g, 0.035 mol) was heated to 240° C. over the course of 3 h with the introduction of nitrogen and the mixture was then stirred at this temperature and the water formed was continuously removed until an acid value of ≤1.0 was reached.

Figure 1:
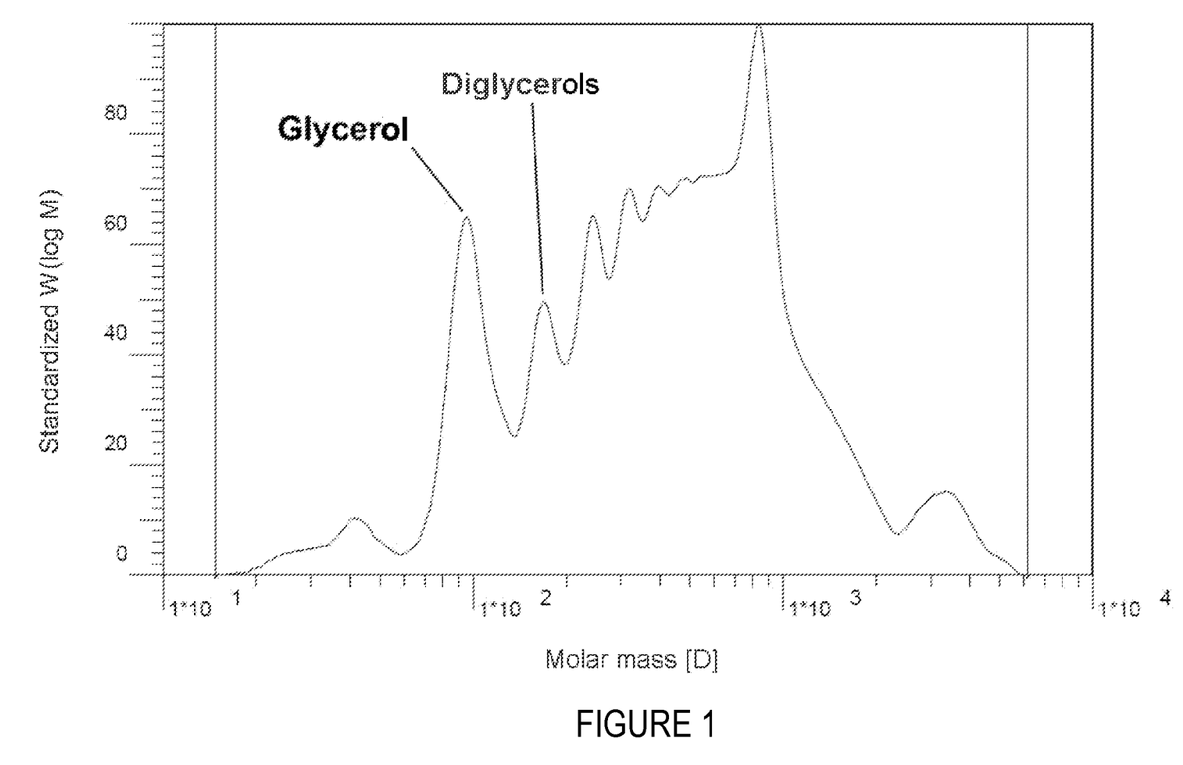
FIG. 1 is a GPC chromatogram of a polyglycerol fraction of a polyglycerol ester according to the invention with particular oligomer distribution of the polyglycerol following alkaline hydrolysis and removal of the fatty acids as described in Example 1.

A GPC chromatogram of the polyglycerol ester obtained in this way after its alkaline cleavage and removal of the fatty acids is shown in FIG. 1.

Example 2

A mixture of glycerol (2102 g, 22.8 mol) and 45% strength aqueous potassium hydroxide solution (24.2 g) was heated to 240° C. at 400 mbar over the course of 1 hour and the water formed was continuously distilled off. As soon as the reaction mixture had achieved a refractive index of ≥1.4900 (typically after 20-21 h at 240° C.), the pressure was slowly lowered to 50 mbar and further water and excess glycerol were distilled off at 240° C. until the remaining mixture had a hydroxyl value of 880 mg KOH/g.

A mixture of the polyglycerol obtained in this way (310.5 g, 0.38 mol) and glycerol (41.25 g, 0.45 mol) with a hydroxyl value of 1000 mg KOH/g and also behenic acid (481.9 g, 1.40 mol) and $Na_2CO_3$ (4.17 g, 0.039 mol) was heated to 240° C. over the course of 3 h with the introduction of nitrogen and the mixture was stirred at this temperature and the water formed was continuously removed until an acid value of ≤1.0 was reached.

Example 3

A mixture of glycerol (2102 g, 22.8 mol) and 45% strength aqueous potassium hydroxyl solution (24.2 g) was heated to 240° C. at 400 mbar over the course of 1 hour and the water formed was continuously distilled off. As soon as the reaction mixture had reached a refractive index of ≥1.4900 (typically after 20-21 h at 240° C.), the pressure was slowly lowered to 50 mbar and further water and excess glycerol were distilled off at 240° C. until the remaining mixture had a hydroxyl value of 880 mg KOH/g.

A mixture of the polyglycerol thus obtained (337.8 g, 0.42 mol) and glycerol (44.87 g, 0.49 mol) with a hydroxyl value of 1000 mg KOH/g and a mixture of stearic acid and palmitic acid in the ratio 1:1 (334.19 g, 1.24 mol) and $Na_2CO_3$ (3.58 g, 0.034 mol) was heated to 240° C. over the course of 3 h under nitrogen introduction and the mixture was then stirred at this temperature and the water formed was continuously removed until an acid value of ≤1.0 was reached.

Example 4

A mixture of a polyglycerol ester obtained as described in Example 2 (5.9 g) and of a polyglycerol ester obtained as described in Example 3 (89.9 g) was heated to 75° C. and stirred at this temperature for 1 h.

Example 5

Not According to the Invention

A mixture of glycerol (2102 g, 22.8 mol) and 45% strength aqueous potassium hydroxide solution (24.2 g) was heated to 240° C. at 400 mbar over the course of 1 hour and the water formed was continuously distilled off. As soon as the reaction mixture had reached a refractive index of ≥1.485, the pressure was slowly lowered to 50 mbar and further water and excess glycerol were distilled off at 240° C. until the remaining mixture had a hydroxyl value of 1000 mg KOH/g and a mass ratio of glycerol to diglycerol of 0.3.

A mixture of the polyglycerol thus obtained (407.82 g, 1.00 mol) and a mixture of stearic acid and palmitic acid in the ratio 1:1 (334.19 g, 1.24 mol), behenic acid (28.0 g, 0.08 mol) and $Na_2CO_3$ (3.75 g, 0.035 mol) was heated to 240° C. over the course of 3 h under nitrogen introduction and the mixture was then stirred at this temperature and the water formed was continuously removed until an acid value of ≤1.0 was reached.

Figure 2:
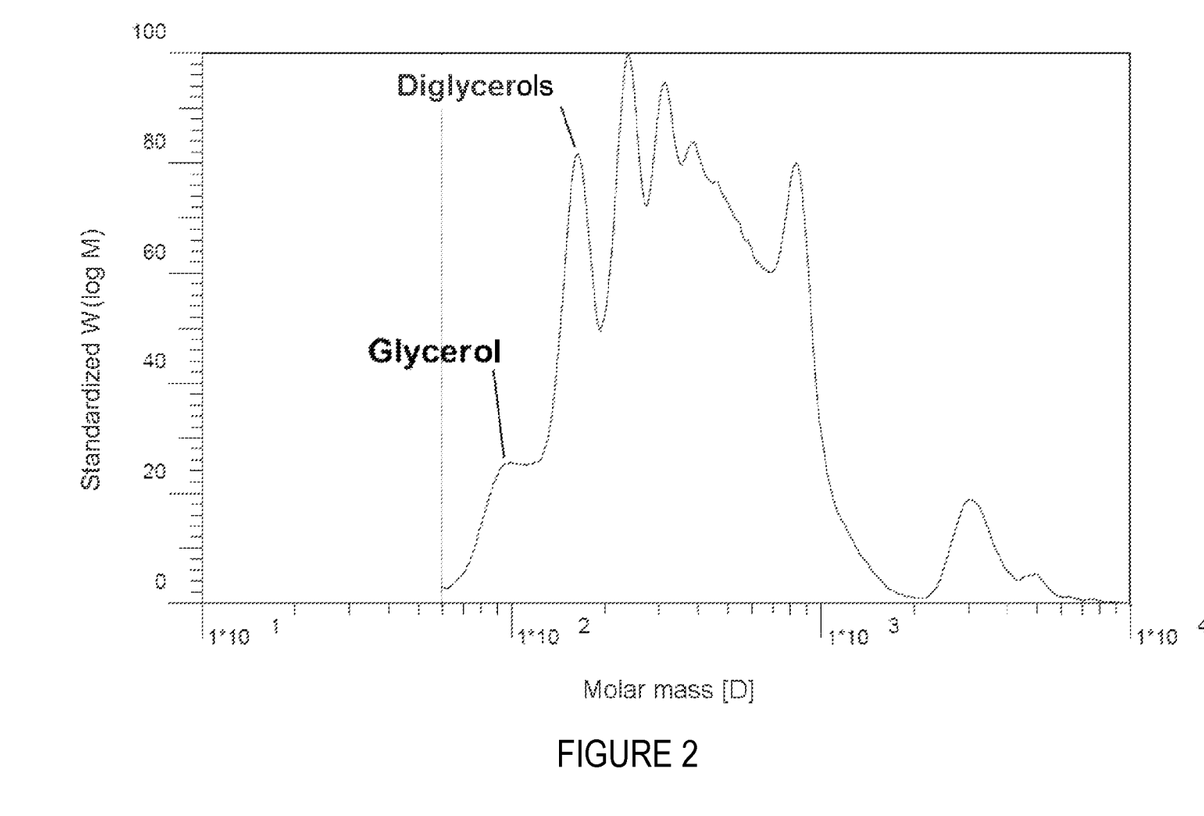
FIG. 2 is a GPC chromatogram of a polyglycerol fraction of a polyglycerol ester not according to the invention with a normal oligomer distribution following alkaline hydrolysis and removal of the fatty acids as described in Example 5.

A GPC chromatogram of the polyglycerol ester obtained in this way after its alkaline cleavage and removal of the fatty acids is shown in FIG. 2.

Example 6

Influence of the Particular Oligomer Distribution of the Polyglycerol Differentiation of the Performance Compared with the Prior Art All concentrations in the application examples are given in percentages by weight. Customary homogenization processes known to the person skilled in the art were used to produce the emulsions.

The emulsions were therefore typically produced by heating oil phase and water phase to 70-75° C. Then, either the oil phase was stirred into the water or the oil phase and water phase were combined without stirring. A suitable homogenizer (e.g., Ultraturrax) was then used to homogenize the mixture for ca. 1-2 minutes.

Stabilizing polymers (e.g. carbomers) are preferably stirred into the emulsion as oil dispersion at temperatures of 50-60° C. Brief homogenization was then carried out.

The addition of further ingredients (e.g. preservatives, active ingredients) was preferably carried out at 40° C. If the formulations were preserved with organic acids, the pH of the emulsions was adjusted to ca. 5.

These experiments are intended to show that the polyglycerol esters according to the invention have advantages with regard to emulsion stability. As a representative of polyglycerol-based O/W emulsifiers based on the prior art, the non-inventive emulsifier from Example 5 was selected.

To test the storage stability of the emulsions, these were stored for three months at room temperature, 40° C. and 45° C. To test the low-temperature stability, moreover, storage for one month at −5° C. and three freeze-thaw cycles of 25° C./−15° C./25° C. were carried out. Significant changes in the appearance or the consistency, and in particular oil or water separations, were weighted as criteria for instability.

Comparison of emulsifiers 1 and 4 according to the invention compared with non-inventive emulsifier 5 in various formulations: 1—lotion with natural preservative, 2—lotion with electrolyte additive, 3—lotion with addition of water-soluble UV filter.

|  | Formulation | | |
| --- | --- | --- | --- |
|  | 1-1 | 1-2 | C1 |
| Emulsifier 1 | 3.0% | | |
| Emulsifier 4 | | 3.0% | |
| Emulsifier 5 (non-inventive) | | | 3.0% |
| GlycerylStearate | 0.4% | 0.4% | 0.4% |
| StearylAlcohol | 0.4% | 0.4% | 0.4% |
| C12-15 Alkyl Benzoate | 3.7% | 3.7% | 3.7% |
| Caprylic/CapricTriglyceride | 3.7% | 3.7% | 3.7% |
| Isopropyl Palmitate | 3.7% | 3.7% | 3.7% |
| Glycerin | 5.0% | 5.0% | 5.0% |
| Demineralized Water | ad 100% | ad 100% | ad 100% |
| Xanthan Gum[1] | 0.5% | 0.5% | 0.5% |
| Sodium hydroxide (10% aq., pH value adjustment to 5.0) | q.s. | q.s. | q.s. |
| Benzyl Alcohol, Benzoic Acid, SorbicAcid[2] | 1.0% | 1.0% | 1.0% |
| Consistency after preparation | Liquid-pasty | Liquid-pasty | Liquid-pasty |
| Stability | Stable | Stable | Water separation after 1 month at 45° C. |

[1] Keltrol CG-SFT (CP Kelco)
[2] Optiphen BSB-N/Rokonsal BSB-N (Ashland Specialty Ingredients)

|  | Formulation | | |
| --- | --- | --- | --- |
|  | 2-1 | 2-2 | C2 |
| Emulsifier 1 | 3.0% | | |
| Emulsifier 4 | | 3.0% | |
| Emulsifier 5 (non-inventive) | | | 3.0% |
| GlycerylStearate | 0.4% | 0.4% | 0.4% |

| | Formulation | | |
|---|---|---|---|
| | 2-1 | 2-2 | C2 |
| StearylAlcohol | 0.4% | 0.4% | 0.4% |
| C12-15 Alkyl Benzoate | 5.4% | 5.4% | 5.4% |
| Caprylic/CapricTriglyceride | 5.4% | 5.4% | 5.4% |
| Isopropyl Palmitate | 5.4% | 5.4% | 5.4% |
| Glycerin | 5.0% | 5.0% | 5.0% |
| Sodium Chloride | 1.0% | 1.0% | 1.0% |
| Demineralized water | ad 100% | ad 100% | ad 100% |
| Xanthan Gum[1] | 0.5% | 0.5% | 0.5% |
| Methylisothiazolinone, Methylparaben, Ethylparaben; Dipropylene Glycol[3] | 0.8 | 0.8 | 0.8 |
| Consistency after preparation | Liquid-pasty | Liquid-pasty | Liquid-pasty |
| Stability | Stable | Stable | Water separation after 1 month at 45° C. |

[3] Microcare ® MEM (Thor)

| | Formulation | | |
|---|---|---|---|
| | 3-1 | 3-2 | C3 |
| Emulsifier 1 | 4.0% | | |
| Emulsifier 4 | | 4.0% | |
| Emulsifier 5 (non-inventive) | | | 4.0% |
| GlycerylStearate | 0.5% | 0.5% | 0.5% |
| StearylAlcohol | 0.5% | 0.5% | 0.5% |
| C12-15 Alkyl Benzoate | 5.0% | 5.0% | 5.0% |
| Caprylic/CapricTriglyceride | 5.0% | 5.0% | 5.0% |
| Isopropyl Palmitate | 5.0% | 5.0% | 5.0% |
| Glycerin | 5.0% | 5.0% | 5.0% |
| Demineralized water | ad 100% | ad 100% | ad 100% |
| Xanthan Gum[1] | 0.3% | 0.3% | 0.3% |
| UV filter solution[4] | 20.0% | 20.0% | 20.0% |
| Methylisothiazolinone, Methylparaben, Ethylparaben; Dipropylene Glycol[3] | 0.8% | 0.8% | 0.8% |
| Consistency after preparation | Thin-liquid to medium viscosity | Thin-liquid to medium viscosity | Thin-liquid |
| Stability | Stable | Stable | Water separation after 1 month at 45° C. |

[4] 10% Phenylbenzimidazolesulphonic acid, 1.4% sodium hydroxide, ad 100% water

Whereas the formulations with emulsifiers 1 and 4 according to the invention in each case leads to a storage-stable formulation, the creams with the non-inventive comparison emulsifier from Example 5 exhibit considerable weaknesses in the storage stability.

Comparison of Emulsifiers According to the Invention Compared with Non-Inventive Emulsifiers in a Sunscreen Lotion in Combination with Insect Repellents.

The non-inventive emulsifiers are typical representatives which are used in standard commercial products of this application type. The respective emulsifiers were used in the formulations with customary use concentrations, the viscosity of the emulsions being adjusted with consistency to the viscosity of a thin-liquid lotion by varying the consistency regulator.

| | Formulation | | | |
|---|---|---|---|---|
| | 4-1 etc. | Z-2 | Z-C1 | Z-C2 |
| Emulsifier 1 | 3.0 | — | — | — |
| Emulsifier 4 | — | 3.0 | — | — |
| Polyglyceryl-3 methylglucosedistearate[a] | — | — | 3.0 | — |
| Polyglyceryl-3 Dicitrate/stearate[b] | — | — | — | 3.0 |
| Glyceryl stearate | 0.5 | 0.5 | — | — |
| Stearylalcohol | 0.5 | 0.5 | — | — |
| Phenoxyethylcaprylate[c] | 2.3 | 2.3 | 3.3 | 3.3 |
| Butyl Methoxydibenzoylmethane | 5.0 | 5.0 | 5.0 | 5.0 |
| Diethylhexylbutamidotriazone | 0.7 | 0.7 | 0.7 | 0.7 |
| Ethylhexylsalicylate | 0.5 | 0.5 | 0.5 | 0.5 |
| Octocrylene | 6.0 | 6.0 | 6.0 | 6.0 |
| Bis-ethylhexyloxyphenolMethoxyphenylthazine[d] | 1.5 | 1.5 | 1.5 | 1.5 |
| Ethyl Butylacetylaminopropionate[e] | 4.0 | 4.0 | 4.0 | 4.0 |
| Tocopherylacetate | 0.5 | 0.5 | 0.5 | 0.5 |
| Nylon 10/10[f] | 0.5 | 0.5 | 0.5 | 0.5 |
| Water | ad 100 | ad 100 | ad 100 | ad 100 |
| Glycerin | 2.0 | 2.0 | 2.0 | 2.0 |
| Hydroxyethylcellulose[g] | 0.5 | 0.5 | 0.5 | 0.5 |
| Methylene bis-benzotriazolylTetramethylbutylphenol (50% aq.)[h] | 11.0 | 11.0 | 11.0 | 11.0 |
| Dipropylene glycol; Methylparaben; ethylparaben; aqua; methylisothiazolinone[3] | 0.8 | 0.8 | 0.8 | 0.8 |
| Consistency after preparation | Low viscosity lotion | Low viscosity lotion | Low viscosity lotion | Low viscosity lotion |

|  | Formulation | | | |
| --- | --- | --- | --- | --- |
|  | 4-1 etc. | Z-2 | Z-C1 | Z-C2 |
| Stability | Stable | Stable | Oil separation after storage for 2 weeks at 45° C. | Oil separation after storage for 2 weeks at 45° C. |

[a] corresponds to [27]
[b] corresponds to [21]
[c] TEGOSOFT XC (Evonik Industries AG) corresponds to [9]
[d] (Tinosorb S, BASF SE) corresponds to [8]
[e] (Insect repellent IR 3535, Merck)
[f] (TEGOLON ECO 10-10, Evonik Industries AG) corresponds to [33]
[g] (Natrosol HHR 250, Ashland Specialty Chemicals)
[h] (Tinosorb M, BASF SE) corresponds to [39]

| | Formulation | | | |
| --- | --- | --- | --- | --- |
|  | Z-C3 | Z-C4 | Z-05 | Z-C6 |
| GlycerylStearate Citrate[i] | 2.0 | — | — | — |
| Polyglyceryl-10 Stearate[j] | — | 3.0 | — | — |
| Polyglyceryl-6 Distearate[k] | — | — | 3.0 | — |
| CetearylGlucoside[l] | — | — | — | 1.5 |
| GlycerylStearate | 1.0 | 1.5 | 0.5 | 0.8 |
| StearylAlcohol | 1.0 | 1.3 | 0.5 | 1.0 |
| PhenoxyethylCaprylate[c] | 2.3 | 0.5 | 2.3 | 3.0 |
| Butyl Methoxydibenzoylmethane | 5.0 | 5.0 | 5.0 | 5.0 |
| DiethylhexylButamidoTriazone | 0.7 | 0.7 | 0.7 | 0.7 |
| EthylhexylSalicylate | 0.5 | 0.5 | 0.5 | 0.5 |
| Octocrylene | 6.0 | 6.0 | 6.0 | 6.0 |
| Bis-EthylhexyloxyphenolMethoxyphenylTriazine[d] | 1.5 | 1.5 | 1.5 | 1.5 |
| Ethyl Butylacetylaminopropionate[e] | 4.0 | 4.0 | 4.0 | 4.0 |
| TocopherylAcetate | 0.5 | 0.5 | 0.5 | 0.5 |
| Nylon 10/10[f] | 0.5 | 0.5 | 0.5 | 0.5 |
| Water | ad 100 | ad 100 | ad 100 | ad 100 |
| Glycerin | 2.0 | 2.0 | 2.0 | 2.0 |
| Hydroxyethylcellulose[g] | 0.5 | 0.5 | 0.5 | 0.5 |
| Methylene bis-BenzotriazolylTetramethylbutylphenol (50% aq.)[h] | 11.0 | 11.0 | 11.0 | 11.0 |
| Dipropylene Glycol; methylparaben; Ethylparaben; Aqua; Methylisothiazolinone[3] | 0.8 | 0.8 | 0.8 | 0.8 |
| Consistency after preparation | Low viscosity lotion | Low viscosity lotion | Low viscosity lotion | Low viscosity lotion |
| Stability | Oil separation after storage for 2 weeks at 45° C. | Oil separation after storage for 2 weeks at 45° C.; viscosity increase (pasty consistency after storage for 1 month at RT) | Oil separation after storage for 2 days at 45° C. | Oil separation after storage for 2 weeks at 45° C. |

[i] corresponds to [7]
[j] Polyaldo 10-1-S KFG (Lonza)
[k] PlurolStearique WL 1009 (Gattefossesas)
[l] corresponds to [5]

| | Formulation | | |
|---|---|---|---|
| | Z-C7 | Z-C8 | Z-C9 |
| Sodium Stearoyl-glutamate[m] | 1.5 | — | — |
| Sodium CetearylSulphate[n] | — | 1.0 | — |
| Potassium CetylPhosphate[o] | — | — | 1.5 |
| Glycerylstearate | 1.0 | 0.4 | 0.6 |
| StearylAlcohol | 1.2 | 0.4 | 0.6 |
| PhenoxyethylCaprylate[c] | 2.6 | 4.5 | 3.6 |
| Butyl methoxydibenzoylmethane | 5.0 | 5.0 | 5.0 |
| DiethylhexylButamido-Triazone | 0.7 | 0.7 | 0.7 |
| EthylhexylSalicylate | 0.5 | 0.5 | 0.5 |
| Octocrylene | 6.0 | 6.0 | 6.0 |
| Bis-Ethylhexyloxyphenol-Methoxyphenyltriazine[d] | 1.5 | 1.5 | 1.5 |
| Ethyl Butylacetylamino-propionate[e] | 4.0 | 4.0 | 4.0 |
| TocopherylAcetate | 0.5 | 0.5 | 0.5 |
| Nylon 10/10[f] | 0.5 | 0.5 | 0.5 |
| Water | ad 100 | ad 100 | ad 100 |
| Glycerin | 2.0 | 2.0 | 2.0 |
| Hydroxyethylcellulose[g] | 0.5 | 0.5 | 0.5 |
| Methylene bis-BenzotriazolylTetramethyl-butylphenol (50% aq.)[h] | 11.0 | 11.0 | 11.0 |
| Dipropylene glycol; methylparaben; ethylparaben; aqua; methylisothiazolinone[3] | 0.8 | 0.8 | 0.8 |
| Consistency after preparation | Low viscosity lotion | Low viscosity lotion | Low viscosity lotion |
| Stability | Oil separation after storage for 2 weeks at 45° C. | Oil separation after storage at 45° C. or 40° C. Phase separation after storage for 1 month at −5° C. or after 3 cycles −15° C./RT | Oil separation after storage for 2 weeks at 45° C. or 40° C. oil separation after storage for 1 month at −5° C. |

[m]corresponds to[12]
[n]corresponds to[16]
[o]Amphisol K (DSM Nutritional Products Inc.)

Whereas formulations Z1 and Z2 with emulsifiers 1 and 4 according to the invention in each case leads to a storage-stable formulation, the lotions with the non-inventive comparative emulsifiers (Z-C1 to Z-C9) exhibit clear weaknesses in the storage stability.

Formulation Examples

These examples are intended to show that the polyglycerol esters according to the invention can be used in a multitude of cosmetic formulations.

Moreover, with the help of the polyglycerol esters according to the invention, it is possible to stably incorporate pigments or solids into emulsion preparations.

Furthermore, the examples exhibit good compatibility with typical coemulsifiers, oils, thickeners and stabilizers, and also good compatibility with emulsion-burdening ingredients such as UV filters, antimicrobial active ingredients or cosmetic active ingredients.

| | Formulation | | |
|---|---|---|---|
| | 4-1 | 4-2 | 4-3 |
| Emulsifier 1 | 3.0% | | 2.5% |
| Emulsifier 4 | | 3.0% | |
| CetearylGlucoside[5] | | | 0.5% |
| GlycerylStearate | 0.2% | 0.2% | 0.2% |
| StearylAlcohol | 0.2% | 0.2% | 0.2% |
| Prunus AmygdalusDulcis (Sweet Almond) oil | 10.0% | 10.0% | 10.0% |
| IsoamylCocoate[6] | 6.6% | 6.6% | 6.6% |
| Glycerin | 4.0% | 4.0% | 4.0% |
| Demineralized Water | ad 100% | ad 100% | ad 100% |
| Xanthan Gum[1] | 0.5% | 0.5% | 0.5% |
| Sodium Hydroxide (10% aq.) (pH adjustment to 5.0) | q.s. | q.s. | q.s. |
| Benzyl Alcohol, Benzoic Acid, SorbicAcid[2] | 1.0% | 1.0% | 1.0% |

[5]TEGO Care CG 90 (Evonik Industries AG)
[6]TEGOSOFT AC (Evonik Industries AG)

Sunscreen Spray

| | Formulation | | |
|---|---|---|---|
| | 5-1 | 5-2 | 5-3 |
| Emulsifier 1 | 3.0% | | |
| Emulsifier 4 | | 3.0% | 2.5% |
| GlycerylStearate Citrate[7] | | | 0.5% |
| GlycerylStearate | 0.5% | 0.5% | 0.5% |
| StearylAlcohol | 0.5% | 0.5% | 0.5% |
| Bis-Ethylhexyloxyphenol-MethoxyphenylTriazine[8] | 3.0% | 3.0% | 3.0% |
| Butyl Methoxydibenzoylmethane | 2.0% | 2.0% | 2.0% |
| EthylhexylMethoxycinnamate | 2.0% | 2.0% | 2.0% |
| EthylhexylSalicylate | 4.0% | 4.0% | 4.0% |
| Octocrylene | 4.0% | 4.0% | 4.0% |
| Isopropyl Palmitate | 2.0% | 2.0% | 2.0% |
| PhenoxyethylCaprylate[9] | 3.2% | 3.2% | 3.2% |
| Glycerin | 3.0% | 3.0% | 3.0% |
| Demineralized Water | ad 100% | ad 100% | ad 100% |
| CarbomerSuspension[10] | 1.0% | 1.0% | 1.0% |
| Tromethamine (30% strength) | 0.9% | 0.9% | 0.9% |
| UV filter solution[11] | 10.0% | 10.0% | 10.0% |
| Methylisothiazolinone, Methylparaben, Ethylparaben; DipropyleneGlycol 4)[3] | 0.8 | 0.8 | 0.8 |

[7]AXOL C 62 (Evonik Industries AG)
[8]Tinosorb S (BASF SE)
[9]TEGOSOFT XC (Evonik Industries AG)
[10]Acrylates/C10-30 alkyl acrylate crosspolymer (TEGO Carbomer 341ER) 20% strength in phenoxyethylcaprylate
[11]20% Phenylbenzimidazolesulphonicacid, 8.8% tris (hydroxymethyl)aminomethane, demineralized water ad 100%

Antiperspirant/Deodorant Lotion

| | Formulation | | |
|---|---|---|---|
| | 6-1 | 6-2 | 6-3 |
| Emulsifier 1 | 3.0% | | 2.5% |
| Emulsifier 4 | | 3.0% | |
| Sodium StearoylGlutamate[12] | | | 0.5% |
| DiethylhexylCarbonate[13] | 3.0% | 3.0% | 3.0% |
| PPG-14 Butyl Ether | 3.0% | 3.0% | 3.0% |
| Polyglyceryl-3 Caprylate | 0.5% | 0.5% | 0.5% |
| Demineralized Water | ad 100% | ad 100% | ad 100% |
| Hydroxyethylcellulose[14] | 1.0% | 1.0% | 1.0% |

-continued

| | Formulation | | |
|---|---|---|---|
| | 6-1 | 6-2 | 6-3 |
| Aluminium Chlorohydrate (50% strength)[15] | 15.0% | 15.0% | 15.0% |
| Methylisothiazolinone, Methylparaben, Ethylparaben; DipropyleneGlycol[3] | 0.8% | 0.8% | 0.8% |

[12] Eumulgin SG (BASF SE)
[13] TEGOSOFT DEC (Evonik Industries AG)
[14] Natrosol 250 HHR (Ashland Specialty Chemicals)
[15] Reach 501L (Reheis)

Antiperspirant/Deodorant Cream

| | Formulation | | |
|---|---|---|---|
| | 7-1 | 7-2 | 7-3 |
| Emulsifier 1 | 3.0% | | |
| Emulsifier 4 | | 3.0% | 2.5% |
| Sodium CetearylSulfate[16] | | | 0.5% |
| GlycerylStearate | 1.0% | 1.0% | 1.0% |
| StearylAlcohol | 1.0% | 1.0% | 1.0% |
| PPG-15 StearylEther | 5.0% | 5.0% | 5.0% |
| IsoamylCocoate[6] | 5.0% | 5.0% | 5.0% |
| DiethylhexylCarbonate[13] | 5.0% | 5.0% | 5.0% |
| PerseaGratissima (Avocado) Oil | 2.0% | 2.0% | 2.0% |
| Polyglyceryl-3 Caprylate | 0.5% | 0.5% | 0.5% |
| Zinc Ricinoleate | 1.0% | 1.0% | 1.0% |
| Demineralized Water | ad 100% | ad 100% | ad 100% |
| Hydroxyethylcellulose[14] | 1.0% | 1.0% | 1.0% |
| AluminumChlorohydrate (50% strength)[15] | 15.0% | 15.0% | 15.0% |
| Methylisothiazolinone, Methylparaben, Ethylparaben; DipropyleneGlycol[3] | 0.8% | 0.8% | 0.8% |

[16] Lanette E (BASF SE)

Lotions with Cosmetic Active Ingredients

| | Formulation | | | | | |
|---|---|---|---|---|---|---|
| | 8-1 | 8-2 | 8-3 | 9-1 | 9-2 | 9-3 |
| Emulsifier 1 | 3.5% | | | 3.5% | | 3.0% |
| Emulsifier 4 | | 3.5% | 2.5% | | 3.5% | |
| Polyglyceryl-10 Stearate | | | 0.5% | | | |
| Stearic Acid | | | | | | 0.5% |
| GlycerylStearate | 0.5% | 0.5% | 0.5% | 0.6% | 0.6% | 0.6% |
| CetearylAlcohol | 0.5% | 0.5% | 0.5% | 0.6% | 0.6% | 0.6% |
| Caprylic/CapricTriglyceride | 8.5% | 8.5% | 8.5% | 8.5% | 8.5% | 8.5% |
| EthylhexylPalmitate[17] | 8.5% | 8.5% | 8.5% | 8.5% | 8.5% | 8.5% |
| Demineralized Water | ad 100% | ad 100% | ad 100% | ad 100% | ad 100% | ad 100% |
| Xanthan Gum[1] | 0.8% | 0.8% | 0.8% | 0.8% | 0.8% | 0.8% |
| Terminalia Arjuna Bark Extract; Pentyleneglycol (proposed)[18] | | | | 2.0% | 2.0% | 2.0% |
| Betaine; Urea; Potassium Lactate; Sodium Polyglutamate (proposed); HydrolyzedSclerotium Gum[19] | 5.0% | 5.0% | 5.0% | | | |
| Phenoxyethanol, Methylparaben, Ethylparaben, Propylparaben[20] | 1.0% | 1.0% | 1.0% | | | |
| Methylisothiazolinone, Methylparaben, Ethylparaben; DipropyleneGlycol[3] | | | | 0.8% | 0.8% | 0.8% |

[17] TEGOSOFT OP (Evonik Industries AG)
[18] TEGO Arjuna S (Evonik Industries AG)
[19] TEGO Smooth (Evonik Industries AG)
[20] Phenonip XB (Clariant International Ltd.)

Lotion with a Low Oil Phase Content

| | Formulation | | |
|---|---|---|---|
| | 10-1 | 10-2 | 10-3 |
| Emulsifier 1 | 3.0% | | 2.0% |
| Emulsifier 4 | | 3.0% | |
| Polyglyceryl-3 dicitrate/stearate[21] | | | 1.0% |
| Cetearylalcohol | 0.5% | 0.5% | 0.5% |
| Caprylic/caprictriglyceride | 6.5% | 6.5% | 6.5% |
| Demineralized water | ad 100% | ad 100% | ad 100% |
| Xanthan Gum[1] | 0.5% | 0.5% | 0.5% |
| Methylisothiazolinone, methylparaben, ethylparaben; dipropyleneglycol[3] | 0.8% | 0.8% | 0.8% |

[21] TEGO Care PSC 3 (Evonik Industries AG)

O/W Sera 1

| | Formulation | | | | |
|---|---|---|---|---|---|
| | 11-1 | 11-2 | 11-3 | 12-1 | 12-2 |
| Emulsifier 1 | 2.5% | | | 4.0% | |
| Emulsifier 4 | | 2.5% | 2.5% | | 4.0% |
| Sodium StearoylGlutamate[12] | | | 1.0% | | |
| CetearylGlucoside[5] | | | | | |
| Polyglyceryl-3 Dicitrate/stearate[21] | | | | | |
| GlycerylStearate | | | | 0.75% | 0.75% |
| StearylAlcohol | | | | 0.75% | 0.75% |
| Caprylic/CapricTriglyceride | 2.0% | 2.0% | 2.0% | 2.0% | 2.0% |
| OleylErucate[22] | 2.0% | 2.0% | 2.0% | 2.0% | 2.0% |
| IsoamylCocoate[6] | | | | 3.0% | 3.0% |
| PerseaGratissima (Avocado) Oil | 1.0% | 1.0% | 1.0% | 1.0% | 1.0% |
| Aqua; Ethylhexyl Stearate; Sodium HyaluronateCrosspolymer; Polyglyceryl-4 Diisostearate/Polyhydroxystearate/Sebacate; Sodium Isostearate[23] | 3.0% | 3.0% | 3.0% | | |

| | Formulation | | | | |
|---|---|---|---|---|---|
| | 11-1 | 11-2 | 11-3 | 12-1 | 12-2 |
| Demineralized Water | ad 100% | ad 100% | ad 100% | ad 100% | ad 100% |
| Butylene Glycol | 5.0% | 5.0% | 5.0% | 5.0% | 5.0% |
| Tetrapeptide-21; Glycerin; Butylene Glycol; Aqua[24] | 2.0% | 2.0% | 2.0% | 2.0% | 2.0% |
| Hydrolyzed Hyaluronic Acid[25] | 0.1% | 0.1% | 0.1% | 0.1% | 0.1% |
| Xanthan Gum[1] | 0.5% | 0.5% | 0.5% | 0.5% | 0.5% |
| Sodium Hydroxide (10% aq.) | 0.2% | 0.2% | 0.2% | 0.2% | 0.2% |
| Benzyl Alcohol, Benzoic Acid, Sorbic Acid[2] | 0.8% | 0.8% | 0.8% | 0.8% | 0.8% |
| Polyglutamic acid; SclerotiumGlucan; Betaine; Urea; Potassium Lactate[26] | 3.0% | 3.0% | 3.0% | 3.0% | 3.0% |

[22] TEGOSOFT OER (Evonik Industries AG)
[23] Hyacare Filler CL (Evonik Industries)
[24] TEGO PEP 4-17 (Evonik Industries)
[25] Hyacare 50 (Evonik Industries)
[26] TEGO Smooth Complex (Evonik Industries)

O/W Sera 2

| | Formulation | | | |
|---|---|---|---|---|
| | 12-3 | 13-1 | 13-2 | 13-3 |
| Emulsifier 1 | 3.0% | 3.0% | | 2.0% |
| Emulsifier 4 | | | 3.0% | |
| Sodium Stearoyl Glutamate[12] | | | | |
| Cetearyl Glucosides[5] | 0.5% | | | |
| Polyglyceryl-3 Dicitrate/Stearate[21] | | | | 1.5% |
| Glyceryl Stearate | 0.75% | 0.5% | 0.5% | 0.5% |
| Stearyl Alcohol | 0.75% | 0.5% | 0.5% | 0.5% |
| Caprylic/Capric Triglyceride | 2.0% | 2.0% | 2.0% | 2.0% |
| OleylErucate[22] | 2.0% | 2.0% | 2.0% | 2.0% |
| IsoamylCocoate[6] | 3.0% | | | |
| PerseaGratissima (Avocado) Oil | 1.0% | 1.0% | 1.0% | 1.0% |
| Aqua; Ethylhexyl Stearate; Sodium HyaluronateCrosspolymer; Polyglyceryl-4 Diisostearate/Polyhydroxystearate/Sebacate; Sodium Isostearate[23] | | 3.0% | 3.0% | 3.0% |
| Demineralized Water | ad 100% | ad 100% | ad 100% | ad 100% |
| Butylene Glycol | 5.0% | 5.0% | 5.0% | 5.0% |
| Tetrapeptide-21; Glycerin; Butylene Glycol; Aqua[24] | 2.0% | 2.0% | 2.0% | 2.0% |
| Hydrolyzed Hyaluronic Acid[25] | 0.1% | 0.1% | 0.1% | 0.1% |
| Xanthan Gum[1] | 0.5% | 0.5% | 0.5% | 0.5% |
| Sodium Hydroxide (10% aq.) | 0.2% | 0.2% | 0.2% | 0.2% |
| Benzyl Alcohol, Benzoic Acid, Sorbic Acid[2] | 0.8% | 0.8% | 0.8% | 0.8% |
| Polyglutamic acid; SclerotiumGlucan; Betaine; Urea; Potassium Lactate[26] | 3.0% | | | |

O/W Blemish Balm Lotion

| | Formulation | | |
|---|---|---|---|
| | 14-1 | 14-2 | 14-3 |
| Emulsifier 1 | 4.00% | | 3.00% |
| Emulsifier 4 | | 4.00% | |
| Polyglyceryl-3 MethylglucoseDistearate[27] | | | 1.00% |
| Glyceryl Stearate | 0.75% | 0.75% | 0.75% |
| Stearyl Alcohol | 0.75% | 0.75% | 0.75% |
| Diethylhexyl Carbonate[13] | 7.40% | 7.40% | 7.40% |
| Aqua; Ethylhexyl Stearate; Sodium HyaluronateCrosspolymer; Polyglyceryl-4 Diisostearate/Polyhydroxystearate/Sebacate; Sodium Isostearate[23] | 2.00% | 2.00% | 2.00% |
| EthylhexylMethoxycinnamate | 5.00% | 5.00% | 5.00% |
| DiethylaminoHydroxybenzoyl Hexyl Benzoate[28] | 3.00% | 3.00% | 3.00% |
| Phytosphingosine | 0.10% | 0.10% | 0.10% |
| Hydrolyzed Hyaluronic Acid[25] | 0.10% | 0.10% | 0.10% |
| Tetrapeptide-21; Glycerin; Butylene Glycol; Aqua[24] | 2.00% | 2.00% | 2.00% |
| Demineralized Water | ad 100% | ad 100% | ad 100% |
| Titanium Dioxide[29] | 3.00% | 3.00% | 3.00% |
| Talc | 2.00% | 2.00% | 2.00% |
| Iron Oxide[30] | 0.36% | 0.36% | 0.36% |
| Iron Oxide[31] | 0.12% | 0.12% | 0.12% |
| Iron Oxide[32] | 0.08% | 0.08% | 0.08% |
| IsoamylCocoate[6] | 4.44% | 4.44% | 4.44% |
| PhenoxyethylCaprylate[9] | 4.00% | 4.00% | 4.00% |
| Nylon-10/10[33] | 3.00% | 3.00% | 3.00% |
| Glycerin | 3.00% | 3.00% | 3.00% |
| Xanthan Gum[1] | 0.50% | 0.50% | 0.50% |
| Ethanol | 3.00% | 3.00% | 3.00% |
| Methylisothiazolinone, Methylparaben, Ethylparaben; Dipropylene Glycol[3] | 0.80% | 0.80% | 0.80% |

[27] TEGO Care 450 (Evonik Industries AG)
[28] Uvinul A Plus (BASF SE)
[29] Hombitan AC 360 (Sachtleben)
[30] Unipure Yellow LC 182 (Sensient Technologies)
[31] Unipure Red LC 381 (Sensient Technologies)
[32] Unipure Black LC 989 (Sensient Technologies)
[33] TEGOLON ECO 10-10 (Evonik Industries AG)

Sunscreen Lotion SPF 30

| | Formulation | | |
|---|---|---|---|
| | 15-1 | 15-2 | 15-3 |
| Emulsifier 1 | 3.00% | | |
| Emulsifier 4 | | 3.00% | 2.00% |
| CetearylGlucoside[5] | | | 0.50% |
| PhenoxyethylCaprylate[9] | 8.00% | 8.00% | 8.00% |
| DiethylaminoHydroxybenzoyl Hexyl Benzoate[28] | 6.00% | 6.00% | 6.00% |
| EthylhexylMethoxycinnamate | 8.00% | 8.00% | 8.00% |
| Stearyl Alcohol | 1.00% | 1.00% | 1.00% |
| Glyceryl Stearate | 1.00% | 1.00% | 1.00% |
| Tocopheryl Acetate | 0.50% | 0.50% | 0.50% |
| Glycerin | 2.00% | 2.00% | 2.00% |
| Demineralized Water | ad 100% | ad 100% | ad 100% |

-continued

|  | Formulation | | |
|---|---|---|---|
|  | 15-1 | 15-2 | 15-3 |
| Tromethamine | 0.90% | 0.90% | 0.90% |
| Phenylbenzimidazole Sulfonic Acid | 2.00% | 2.00% | 2.00% |
| Acrylates/C10-30 Alkyl Acrylate Crosspolymer[34] | 0.30% | 0.30% | 0.30% |
| Sodium Hydroxide (10% aq.) | q.s. | q.s. | q.s. |
| Dipropylene Glycol; Methylparaben; Ethylparaben; Aqua; Methylisothiazolinone[3] | 0.80% | 0.80% | 0.80% |

[34] TEGO ® Carbomer 341 ER (Evonik Industries AG)

Sunscreen Lotion SPF 30, High UVA Protection

|  | Formulation | | |
|---|---|---|---|
|  | 16-1 | 16-2 | 16-3 |
| Emulsifier 1 | 3.00% |  |  |
| Emulsifier 4 |  | 3.50% | 2.50% |
| Sodium CetearylSulfate[16] |  |  | 0.50% |
| PhenoxyethylCaprylate[9] | 7.30% | 7.30% | 7.30% |
| Butyl Methoxydibenzoylmethane | 5.00% | 5.00% | 5.00% |
| DiethylhexylButamidoTriazone[35] | 1.00% | 1.00% | 1.00% |
| Ethylhexyl Salicylate | 1.50% | 1.50% | 1.50% |
| Octocrylene | 3.50% | 3.50% | 3.50% |
| Titanium Dioxide; Diethylhexyl Carbonate; Polyglyceryl-6 Polyhydroxystearate[36] | 2.20% | 2.20% | 2.20% |
| Stearyl Alcohol | 1.00% | 1.00% | 1.00% |
| Nylon-10/10[33] | 0.50% | 0.50% | 0.50% |
| Glyceryl Stearate | 1.00% | 1.00% | 1.00% |
| Tocopheryl Acetate | 0.50% | 0.50% | 0.50% |
| Glycerin | 2.00% | 2.00% | 2.00% |
| Demineralized Water | ad 100% | ad 100% | ad 100% |
| Citric Acid (50% aq.) | 0.10% | 0.10% | 0.10% |
| Bis-EthylhexyloxyphenolMethoxyphenyl-Triazine[8] | 20.00% | 20.00% | 20.00% |
| Acrylates/C10-30 Alkyl Acrylate Crosspolymer[34] | 0.30% | 0.30% | 0.30% |
| Sodium Hydroxide (10% a.q.) | 0.90% | 0.90% | 0.90% |
| Dipropylene Glycol; Methylparaben; Ethylparaben; Aqua; Methylisothiazolinone[4] | 0.80% | 0.80% | 0.80% |

[35] UVAsorb HEB (3V Sigma)
[36] TEGO Sun TDEC 45 (Evonik Industries AG)

Sunscreen Lotion SPF 30

|  | Formulation | | |
|---|---|---|---|
|  | 17-1 | 17-2 | 17-3 |
| Emulsifier 1 | 3.00% |  | 2.00% |
| Emulsifier 4 |  | 3.00% |  |
| MethylglucoseSesquistearate[37] |  |  | 1.00% |
| PhenoxyethylCaprylate[9] | 1.50% | 1.50% | 1.50% |
| Octocrylene | 10.00% | 10.00% | 10.00% |
| Butyl Methoxydibenzoylmethane | 3.50% | 3.50% | 3.50% |
| Titanium Dioxide; Diethylhexyl Carbonate; Polyglyceryl-6 Polyhydroxystearate[36] | 14.50% | 14.50% | 14.50% |
| Stearyl Alcohol | 0.20% | 0.20% | 0.20% |
| Glyceryl Stearate | 0.20% | 0.20% | 0.20% |
| Tocopheryl Acetate | 0.50% | 0.50% | 0.50% |
| Glycerin | 2.00% | 2.00% | 2.00% |
| Demineralized Water | ad 100% | ad 100% | ad 100% |
| Acrylates/C10-30 Alkyl Acrylate Crosspolymer[34] | 0.20% | 0.20% | 0.20% |

-continued

|  | Formulation | | |
|---|---|---|---|
|  | 17-1 | 17-2 | 17-3 |
| Sodium Hydroxide (10% aq.) | 0.60% | 0.60% | 0.60% |
| Dipropylene Glycol; Methylparaben; Ethylparaben; Aqua; Methylisothiazolinone[3] | 0.80% | 0.80% | 0.80% |

[37] TEGO Care PS (Evonik Industries AG)

Sunscreen SPF 50, High UVA Protection

|  | Formulation | | |
|---|---|---|---|
|  | 18-1 | 18-2 | 18-3 |
| Emulsifier 1 | 3.00% |  | 2.50% |
| Emulsifier 4 |  | 3.00% |  |
| Polyglyceryl-3 MethylglucoseDistearate[27] |  |  | 0.50% |
| PhenoxyethylCaprylate[9] | 2.00% | 2.00% | 2.00% |
| Nylon-10/10[33] | 0.50% | 0.50% | 0.50% |
| Butyl Methoxydibenzoylmethane | 5.00% | 5.00% | 5.00% |
| DiethylhexylButamidoTriazone[35] | 1.00% | 1.00% | 1.00% |
| Bis-Ethylhexyloxyphenol-MethoxyphenylTriazine[8] | 3.00% | 3.00% | 3.00% |
| Ethylhexyl Salicylate | 1.00% | 1.00% | 1.00% |
| Octocrylene | 8.00% | 8.00% | 8.00% |
| Stearyl Alcohol | 0.45% | 0.45% | 0.45% |
| Glyceryl Stearate | 0.45% | 0.45% | 0.45% |
| Xanthan Gum[1] | 0.30% | 0.30% | 0.30% |
| Tocopheryl Acetate | 0.50% | 0.50% | 0.50% |
| Hydroxyethylcellulose[14] | 0.50% | 0.50% | 0.50% |
| Demineralized Water | ad 100% | ad 100% | ad 100% |
| Sodium Hydroxide (10% aq., pH value adjustment to 7.5) | q.s. | q.s. | q.s. |
| Disodium Phenyl DibenzimidazoleTetrasulfonate[38] | 5.00% | 5.00% | 5.00% |
| Methylene Bis-Benzotriazolyl-Tetramethyl-butylphenol[39] | 8.00% | 8.00% | 8.00% |
| Dipropylene Glycol; Methylparaben; Ethylparaben; Aqua; Methylisothiazolinone[3] | 0.80% | 0.80% | 0.80% |

[38] Neoheliopan AP (Symrise)
[39] Tinosorb M (BASF SE)

Sunscreen Lotion SPF 50

|  | Formulation | | |
|---|---|---|---|
|  | 19-1 | 19-2 | 19-3 |
| Emulsifier 1 | 3.50% |  |  |
| Emulsifier 4 |  | 3.50% | 3.00% |
| Glyceryl Stearate Citrate[7] |  |  | 1.00% |
| PhenoxyethylCaprylate[9] | 2.50% | 2.50% | 2.50% |
| DiethylaminoHydroxybenzoyl Hexyl Benzoate | 10.00% | 10.00% | 10.00% |
| EthylhexylMethoxycinnamate | 10.00% | 10.00% | 10.00% |
| Stearyl Alcohol | 1.00% | 1.00% | 1.00% |
| Glyceryl Stearate | 1.00% | 1.00% | 1.00% |
| Xanthan Gum[1] | 0.50% | 0.50% | 0.50% |
| Tocopheryl Acetate | 0.50% | 0.50% | 0.50% |
| Glycerin | 2.00% | 2.00% | 2.00% |
| Demineralized Water | ad 100% | ad 100% | ad 100% |
| Phenylbenzimidazole Sulfonic Acid | 4.00% | 4.00% | 4.00% |
| Tromethamine | 1.80% | 1.80% | 1.80% |
| Dipropylene Glycol; Methylparaben; Ethylparaben; Aqua; Methylisothiazolinone[3] | 0.80% | 0.80% | 0.80% |

Sunscreen Lotion SPF 50+

| | Formulation | | |
|---|---|---|---|
| | 20-1 | 20-2 | 20-3 |
| Emulsifier 1 | 3.00% | | 2.5% |
| Emulsifier 4 | | 3.00% | |
| Potassium Cetyl Phosphate | | | 1.0% |
| PhenoxyethylCaprylate[9] | 3.00% | 3.00% | 3.00% |
| Butyl Methoxydibenzoylmethane | 5.00% | 5.00% | 5.00% |
| Octocrylene | 4.90% | 4.90% | 4.90% |
| EthylhexylMethoxycinnamate | 0.10% | 0.10% | 0.10% |
| Bis-EthylhexyloxyphenolMethoxyphenylTriazine[8] | 4.70% | 4.70% | 4.70% |
| DiethylhexylButamidoTriazone[35] | 3.70% | 3.70% | 3.70% |
| Titanium Dioxide; Diethylhexyl Carbonate; Polyglyceryl-6 Polyhydroxystearate[36] | 11.00% | 11.00% | 11.00% |
| Stearyl Alcohol | 0.50% | 0.50% | 0.50% |
| Glyceryl Stearate | 0.50% | 0.50% | 0.50% |
| Xanthan Gum[1] | 0.20% | 0.20% | 0.20% |
| Glycerin | 2.00% | 2.00% | 2.00% |
| Demineralized Water | ad 100% | ad 100% | ad 100% |
| Dipropylene Glycol; Methylparaben; Ethylparaben; Aqua; Methylisothiazolinone[3] | 0.80% | 0.80% | 0.80% |

Lotion for Sensitive Skin

| | Formulation | | |
|---|---|---|---|
| | 21 | 22 | 23 |
| Emulsifier 1 | 3.0% | 3.0% | 3.0% |
| Glyceryl Stearate | 0.5% | 1.0% | 0.5% |
| Cetearyl Alcohol | 1.0% | 1.0% | 1.0% |
| *ButyrospermumParkii* (Shea) Butter | 3.0% | 3.0% | 3.0% |
| Caprylic/Capric Triglyceride | 5.0% | 5.0% | 5.0% |
| Isopropyl Palmitate | 5.0% | 5.0% | 5.0% |
| Xanthan Gum[1] | 0.2% | 0.2% | 0.2% |
| Glycerin | 5.0% | 5.0% | 5.0% |
| Urea | 10.0% | 15.0% | 20.0% |
| Demineralized Water | ad 100% | ad 100% | ad 100% |
| Phenoxyethanol, Ethylhexylglycerin[40] | 0.7% | | |
| Sodium Hydroxide (10% aq.) (pH value adjustment to 5.0) | | q.s. | |
| Sodium Benzoate, Potassium Sorbate[41] | | 1.2% | |
| Methylisothiazolinone, Methylparaben, Ethylparaben; Dipropylene Glycol[3] | | | 0.8% |

[40] Euxyl PE 9010 (Schülke & Mayr GmbH)
[41] Euxyl K 712 (Schülke & Mayr GmbH)

Care Lotion for Dry Skin 1

| | Formulation | | | | |
|---|---|---|---|---|---|
| | 24-1 | 24-2 | 24-3 | 25-1 | 25-2 |
| Emulsifier 1 | 3.0% | | | 3.0% | |
| Emulsifier 4 | | 3.0% | 2.5% | | 3.0% |
| Sodium Stearoyl Glutamate[12] | | | 1.0% | | |
| Glyceryl Stearate | 1.0% | 1.0% | 1.0% | 1.5% | 1.5% |
| Cetearyl Alcohol | 1.0% | 1.0% | 1.0% | 1.5% | 1.5% |
| CetylRicinoleate | 2.0% | 2.0% | 2.0% | 2.0% | 2.0% |
| OleylErucate[22] | 5.0% | 5.0% | 5.0% | 5.0% | 5.0% |
| IsoamylCocoate[6] | 8.0% | 8.0% | 8.0% | 8.0% | 8.0% |
| DecylCocoate[42] | 3.0% | 3.0% | 3.0% | 3.0% | 3.0% |
| Xanthan Gum[1] | 0.2% | 0.2% | 0.2% | 0.2% | 0.2% |
| Glycerin | 5.0% | 5.0% | 5.0% | 5.0% | 5.0% |
| Urea | 10.0% | 10.0% | 10.0% | 15.0% | 15.0% |
| Demineralized Water | ad 100% | ad 100% | ad 100% | ad 100% | ad 100% |
| Methylisothiazolinone, Methylparaben, Ethylparaben; Dipropylene Glycol[3] | 0.8% | 0.8% | 0.8% | 0.8% | 0.8% |

[42] TEGOSOFT DC (Evonik Industries AG)

Care Lotion for Dry Skin 2

| | Formulation | | | |
|---|---|---|---|---|
| | 25-3 | 26-1 | 26-2 | 26-3 |
| Emulsifier 1 | | 3.0% | | 3.0% |
| Emulsifier 4 | 2.5% | | 3.0% | |
| Polyglyceryl-6 Distearate | 0.5% | | | |
| Stearic Acid | | | | 0.5% |
| Glyceryl Stearate | 1.5% | 1.5% | 1.5% | 1.5% |
| Cetearyl Alcohol | 1.5% | 1.5% | 1.5% | 1.5% |
| CetylRicinoleate | 2.0% | 2.0% | 2.0% | 2.0% |
| OleylErucate[22] | 5.0% | 5.0% | 5.0% | 5.0% |
| IsoamylCocoate[6] | 8.0% | 8.0% | 8.0% | 8.0% |
| DecylCocoate[42] | 3.0% | 3.0% | 3.0% | 3.0% |
| Xanthan Gum[1] | 0.2% | 0.2% | 0.2% | 0.2% |
| Glycerin | 5.0% | 5.0% | 5.0% | 5.0% |
| Urea | 15.0% | 20.0% | 20.0% | 20.0% |
| Demineralized Water | ad 100% | ad 100% | ad 100% | ad 100% |
| Methylisothiazolinone, Methylparaben, Ethylparaben; Dipropylene Glycol[3] | 0.8% | 0.8% | 0.8% | 0.8% |

[42] TEGOSOFT DC (Evonik Industries AG)

Preservative-Free Lotions 1

| | Formulation | | | | |
|---|---|---|---|---|---|
| | 27-1 | 27-2 | 27-3 | 28-1 | 28-2 |
| Emulsifier 1 | 3.0% | | 2.0% | 3.0% | |
| Emulsifier 4 | | 3.0% | | | 3.0% |
| Glyceryl Stearate Citrate[7] | | | 1.0% | | |
| Glyceryl Stearate SE Polyglyceryl-3 Dicitrate/Stearate[21] | | | | | |
| Glyceryl Stearate | 0.2% | 0.2% | 0.2% | 0.5% | 0.5% |
| Stearyl Alcohol | 0.2% | 0.2% | 0.2% | 0.5% | 0.5% |
| *PrunusAmygdalusDulcis* (Sweet Almond) Oil | 10.0% | 10.0% | 10.0% | 10.0% | 10.0% |
| IsoamylCocoate[6] | 6.6% | 6.6% | 6.6% | 6.0% | 6.0% |
| Glycerin | 4.0% | 4.0% | 4.0% | 4.0% | 4.0% |
| Demineralized Water | ad 100.0% | ad 100.0% | ad 100.0% | ad 100.0% | ad 100.0% |
| Caprylyl Glycol, Glycerin, GlycerylCaprylate, Phenylpropanol[43] | 1.0% | 1.0% | 1.0% | | |

| Formulation | | | | |
|---|---|---|---|---|
| | 27-1 | 27-2 | 27-3 | 28-1 | 28-2 |
| Methylpropanediol, Caprylyl Glycol, Phenylpropanol[44] | | | | 4.0% | 4.0% |
| Xanthan Gum[1] | 0.5% | 0.5% | 0.5% | 0.5% | 0.5% |

[43]Dermosoft LP (Dr. Straetmans Chemische Produkte GmbH)
[44]Dermosoft OMP (Dr. Straetmans Chemische Produkte GmbH)
[45]Dermosoft Octiol (Dr. Straetmans Chemische Produkte GmbH)
[46]Dissolve 3.0 g of sodium hydroxide in 56.5 g of demineralised water, add 30.0 g of glycerin and 10.0 g of DermosoftOctiol (Dr. Straetmans Chemische Produkte GmbH), stir until the solution is clear.

Preservative-Free Lotions 2

| | Formulation | | | |
|---|---|---|---|---|
| | 28-3 | 29-1 | 29-2 | 29-3 |
| Emulsifier 1 | | 3.0% | | 1.5% |
| Emulsifier 4 | 3.0% | | 3.0% | |
| Glyceryl Stearate SE | 0.5% | | | |
| Polyglyceryl-3 Dicitrate/Stearate[21] | | | | 1.5% |
| Glyceryl Stearate | 0.5% | 0.5% | 0.5% | 0.5% |
| Stearyl Alcohol | 0.5% | 0.5% | 0.5% | 0.5% |
| PrunusAmygdalusDulcis (Sweet Almond) Oil | 10.0% | 10.0% | 10.0% | 10.0% |
| IsoamylCocoate[6] | 6.0% | 6.0% | 6.0% | 6.0% |
| Glycerin | 4.0% | 4.0% | 4.0% | 4.0% |
| Demineralized Water | ad 100.0% | ad 100.0% | ad 100.0% | ad 100.0% |
| Methylpropanediol, Caprylyl Glycol, Phenylpropanol[44] | 4.0% | | | |
| Caprylyl Glycol[45] | | 0.4% | 0.4% | 0.4% |
| p-Anisicacid solution 10% strength[46] | | 2.0% | 2.0% | 2.0% |
| Citric Acid (10% aq.) (pH adjustment to 6.0) | | q.s. | q.s. | q.s. |
| Xanthan Gum[1] | 0.5% | 0.5% | 0.5% | 0.5% |

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A polyglycerol ester, wherein after its complete hydrolysis, releases on average (number-average) per mole of polyglycerol ester, carboxylic acids consisting of from 0.01 mol to 0.20 mol of a first fatty acid having 20 to 24 carbon atoms and from 0.5 mol to 2.0 mol of a second fatty acid or a mixture of fatty acids having 8 to 18 carbon atoms, and wherein after complete hydrolysis of the polyglycerol ester, a polyglycerol comprising glycerol and diglycerol is obtained in which a mass ratio of glycerol to diglycerol is greater than 1.

2. The polyglycerol ester according to claim 1, wherein the polyglycerol obtained after complete hydrolysis of the polyglycerol ester has an average degree of polymerization of from 3 to 20.

3. The polyglycerol ester according to claim 1, wherein a molar ratio of the first fatty acid obtained after complete hydrolysis of the polyglycerol ester relative to the second fatty acid is between 1:50 to 1:7.

4. The polyglycerol ester according to claim 3, wherein the first and second fatty acids are selected from linear, saturated, and unsubstituted fatty acids.

5. The polyglycerol ester according to claim 3, wherein the first fatty acid is behenic acid and the second fatty acid is a mixture of stearic acid and palmitic acid.

6. A process for producing the polyglycerol ester of claim 1 comprising:
A) providing a polyglycerol in which a mass ratio of glycerol to diglycerol is greater than 1, and
B) esterifying at least some of the polyglycerol with the carboxylic acids,
where a molar ratio of the carboxylic acids used in process step B) to polyglycerol used in process step A) is from 0.51:1 to 2.20:1.

7. The process according to claim 6, wherein the polyglycerol provided in process step A) has an average degree of polymerization of from 3 to 20.

8. The process according to claim 6, wherein in process step B), the first fatty acid is behenic acid and the second fatty acid is a mixture of stearic acid and palmitic acid.

9. A cosmetic or pharmaceutical formulation comprising:
a polyglycerol ester of claim 1, as an emulsifier, and at least one substance selected from the group consisting of an emollient, a coemulsifier, a thickening agent, an antioxidant, a hydrotrope, a solid or filler, a pearlescent additive, a deodorant ingredient, an antiperspirant active ingredient, an insect repellent, a self-tanning agent, a preservative, a conditioner, a perfume, a dye, a pigment, a cosmetic active ingredient, a care additive, a superfattening agent, a solvent, an UV filter, an electrolyte, a multifunctional additive, and a moisturizer.

10. The cosmetic or pharmaceutical formulation according to claim 9, wherein the polyglycerol ester is present in amounts of from 0.1 to 10% by weight.

11. The cosmetic or pharmaceutical formulation according to claim 10, wherein said at least one substance is a water-soluble UV light protection filter.

12. The cosmetic or pharmaceutical formulation according to claim 11, wherein said at least one substance is an insect repellent.

* * * * *